United States Patent
Cottard et al.

(10) Patent No.: US 7,147,672 B2
(45) Date of Patent: Dec. 12, 2006

(54) OXIDATION DYEING COMPOSITION FOR KERATIN FIBERS COMPRISING A CATIONIC POLY(VINYLLACTAM) AND AT LEAST ONE C10-C14 FATTY ACID, METHODS AND DEVICES FOR OXIDATION DYEING

(75) Inventors: François Cottard, Courbevoie (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/690,696

(22) Filed: Oct. 21, 2003

(65) Prior Publication Data

US 2004/0133995 A1    Jul. 15, 2004

Related U.S. Application Data

(60) Provisional application No. 60/475,489, filed on Jun. 4, 2003.

(30) Foreign Application Priority Data

Oct. 21, 2002   (FR) .................................. 02 13099

(51) Int. Cl.
*A61K 7/13* (2006.01)

(52) U.S. Cl. .................... 8/405; 8/406; 8/407; 8/408; 8/409; 8/410; 8/412; 8/554; 8/558; 8/580; 8/606

(58) Field of Classification Search ............... 8/405, 8/406, 407, 408, 409, 410, 412, 554, 558, 8/580, 606
See application file for complete search history.

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/122 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,528,378 A | 10/1950 | Mannheimer | 260/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,632,559 A | 1/1972 | Matter et al. | 260/78 |
| 3,836,537 A | 9/1974 | Boerwinkle et al. | 260/29.6 |
| 3,874,870 A | 4/1975 | Green et al. | 71/67 |
| 3,910,862 A | 10/1975 | Barabas et al. | 260/79.3 |
| 3,912,808 A | 10/1975 | Sokol | 424/71 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 3,986,825 A | 10/1976 | Sokol | 8/10.1 |
| 4,001,432 A | 1/1977 | Green et al. | 424/329 |
| 4,005,193 A | 1/1977 | Green et al. | 424/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,020 A | 5/1977 | Green et al. | 424/248.56 |
| 4,031,307 A | 6/1977 | DeMartino et al. | 536/114 |
| 4,075,136 A | 2/1978 | Schaper | 260/2 R |
| 4,131,576 A | 12/1978 | Iovine et al. | 260/174 |
| 4,157,388 A | 6/1979 | Christiansen | 424/70 |
| 4,165,367 A | 8/1979 | Chakrabarti | 424/47 |
| 4,166,894 A | 9/1979 | Shaper | 528/271 |
| 4,172,887 A | 10/1979 | Vanlerberghe et al. | 424/70 |
| RE30,199 E | 1/1980 | Rose et al. | 8/10.2 |
| 4,189,468 A | 2/1980 | Vanlerberghe et al. | 424/70 |
| 4,197,865 A | 4/1980 | Jacquet et al. | 132/7 |
| 4,217,914 A | 8/1980 | Jacquet et al. | 132/7 |
| 4,223,009 A | 9/1980 | Chakrabarti | 424/147 |
| 4,240,450 A | 12/1980 | Grollier et al. | 132/7 |
| 4,277,581 A | 7/1981 | Vanlerberghe et al. | 525/420 |
| 4,349,532 A | 9/1982 | Vanlerberghe et al. | 424/47 |
| 4,422,853 A | 12/1983 | Jacquet et al. | 8/406 |
| 4,445,521 A | 5/1984 | Grollier et al. | 132/7 |
| 4,591,610 A | 5/1986 | Grollier | 524/55 |
| 4,608,250 A | 8/1986 | Jacquet et al. | 424/71 |
| 4,702,906 A | 10/1987 | Jacquet et al. | 424/70 |
| 4,719,099 A | 1/1988 | Grollier et al. | 424/47 |
| 4,719,282 A | 1/1988 | Nadolsky et al. | 528/310 |
| 4,761,273 A | 8/1988 | Grollier et al. | 424/47 |
| 4,803,221 A | 2/1989 | Bair | 514/510 |
| 4,839,166 A | 6/1989 | Grollier et al. | 424/71 |

(Continued)

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 080 976 | 6/1983 |

(Continued)

OTHER PUBLICATIONS

English language Derwent Abstract of FR 2 820 032, Aug. 2, 2002.

(Continued)

*Primary Examiner*—Eisa Elhilo
(74) *Attorney, Agent, or Firm*—Finnegan, Henderson, Farabow, Garrett & Dunner LLP

(57) ABSTRACT

A composition for the oxidation dyeing of keratin fibers, for example, human keratin fibers such as hair, comprising, in an appropriate dyeing medium, at least one oxidation dye, at least one fatty acid chosen from $C_{10}$–$C_{14}$ fatty acids and at least one cationic poly(vinyllactam) and dyeing methods and devices using the composition.

56 Claims, No Drawings

U.S. PATENT DOCUMENTS

| | | | |
|---|---|---|---|
| 4,948,579 A | 8/1990 | Jacquet et al. | 424/72 |
| 4,996,059 A | 2/1991 | Grollier et al. | 424/71 |
| 5,009,880 A | 4/1991 | Grollier et al. | 424/47 |
| 5,061,289 A | 10/1991 | Clausen et al. | 8/405 |
| 5,089,252 A | 2/1992 | Grollier et al. | 424/47 |
| 5,139,037 A | 8/1992 | Grollier et al. | 132/703 |
| 5,143,518 A | 9/1992 | Madrange et al. | 8/405 |
| 5,196,189 A | 3/1993 | Jacquet et al. | 424/72 |
| 5,380,340 A | 1/1995 | Neunhoeffer et al. | 8/409 |
| 5,534,267 A | 7/1996 | Neunhoeffer et al. | 424/701 |
| 5,587,155 A * | 12/1996 | Ochiai et al. | 424/70.28 |
| 5,663,366 A | 9/1997 | Neunhoeffer et al. | 248/371.4 |
| 5,766,576 A | 6/1998 | Löwe et al. | 424/62 |
| 5,868,800 A * | 2/1999 | Cotteret et al. | 8/410 |
| 5,958,392 A | 9/1999 | Grollier et al. | 424/70.17 |
| 6,099,592 A | 8/2000 | Vidal et al. | 8/409 |
| 6,099,593 A | 8/2000 | Terranova et al. | 8/409 |
| 6,284,003 B1 | 9/2001 | Rose et al. | 8/412 |
| 6,338,741 B1 | 1/2002 | Vidal et al. | 8/409 |
| 6,645,258 B1 | 11/2003 | Vidal et al. | 8/405 |
| 2002/0046431 A1* | 4/2002 | Laurent et al. | 8/405 |
| 2002/0050013 A1 | 5/2002 | Vidal et al. | 8/405 |
| 2003/0019051 A9 | 1/2003 | Vidal et al. | 8/405 |
| 2003/0192134 A1 | 10/2003 | Desennee et al. | 8/405 |

FOREIGN PATENT DOCUMENTS

| | | |
|---|---|---|
| EP | 01 122 324 A1 | 10/1984 |
| EP | 0 337 354 A1 | 10/1989 |
| EP | 1 179 336 | 2/2002 |
| EP | 1179 336 A1 * | 2/2002 |
| EP | 1 321 134 A2 | 6/2003 |
| FR | 1 400 366 | 4/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 750 048 | 12/1997 |
| FR | 2 820 032 | 8/2002 |
| FR | 2820032 * | 8/2002 |
| GB | 1 021 400 | 3/1966 |
| GB | 1 026 978 | 4/1966 |
| GB | 1 153 196 | 5/1969 |
| GB | 1 546 809 | 5/1979 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 00/68282 | 11/2000 |

OTHER PUBLICATIONS

Co-pending U.S. Appl. No. 10/688,970, filed Oct. 21, 2003.
Co-pending U.S. Appl. No. 10/688,958, filed Oct. 21, 2003.
Office Action in co-pending U.S. Appl. No. 10/688,970, filed Nov. 9, 2004.
Final Office Action in co-pending U.S. Appl. No. 10/290,149, filed Jul. 5, 2005.
Office Action in co-pending U.S. Appl. No. 10/688,958, filed Nov. 9, 2004.
Final Office Action in co-pending U.S. Appl. No. 10/688,958, filed Jul. 5, 2005.
M.R. Porter, BSc, PhD, CChem, MRSC, "Handbook of Surfactants," Blackie & SonsLtd., Glasgow & London, 1991, pp. 116-178.
English language Derwent Abstract of EP 0 080 976, Jun. 8, 1983.
English language abstract of JP 2-19576, Jan. 23, 1990.
English language abstract of JP 9-110659, Apr. 28, 1997.

* cited by examiner

OXIDATION DYEING COMPOSITION FOR KERATIN FIBERS COMPRISING A CATIONIC POLY(VINYLLACTAM) AND AT LEAST ONE C10-C14 FATTY ACID, METHODS AND DEVICES FOR OXIDATION DYEING

This application claims benefit of U.S. Provisional Application No. 60/475,489, filed Jun. 4, 2003.

Disclosed herein is a composition for the oxidation dyeing of keratin fibers, for example, human keratin fibers, such as hair, comprising at least one oxidation dye, at least one particular cationic poly(vinyllactam) and at least one particular fatty acid.

It is a known practice to dye keratin fibers, for example, human hair, with dyeing compositions comprising oxidation dye precursors, generally called "oxidation bases", such as ortho- or para-phenylenediamines, ortho- or para-aminophenols, and heterocyclic bases.

Oxidation dye precursors are compounds, initially only slightly colored or colorless, which develop their dyeing power in the hair in the presence of oxidizing agents, leading to the formation of colored compounds. The formation of these colored compounds may result either from oxidative condensation of the "oxidation bases" with themselves, or oxidative condensation of the "oxidation bases" with color modifying compounds, or "couplers", which are generally present in the dyeing compositions used in oxidation dyeing and are represented, for example, by meta-phenylenediamines, meta-aminophenols and meta-diphenols, and certain heterocyclic compounds.

The variety of molecules used, which comprise, on the one hand, "oxidation bases" and on the other hand, "couplers," allows a very rich palette of colors to be obtained.

To confine the oxidation dyeing product upon application to the hair so that it does not run over the face or outside the areas which it is desired to dye, use has up until now been made of traditional thickeners such as crosslinked polyacrylic acid, hydroxyethyl-celluloses, certain polyurethanes, waxes or mixtures of nonionic surfactants having an HLB (Hydrophilic Lipophilic Balance), suitably chosen, which can produce a gelling effect when they are diluted with water and/or surfactants.

Most of the thickening systems of the prior art may not make it possible to obtain intense and chromatic shades of low selectivity and good fastness and to offer a good cosmetic condition to the treated hair. Moreover, it has been observed that most of the ready-to-use dyeing compositions of the prior art comprising at least one oxidation dye, and a thickening system may not allow a sufficiently precise application without running or drops in viscosity over time.

French Patent Application No. FR 2 820 032 describes ready-to-use oxidation dyeing compositions which do not run and therefore remain well confined to the site of application; these compositions comprise, in an appropriate dyeing medium, at least one oxidation dye, and at least one cationic poly(vinyllactam); these compositions may also make it possible to obtain intense and chromatic (radiant) shades with low selectivities and good fastness towards chemical agents (shampoo, permanent waving and the like) or natural agents (light, perspiration and the like) while offering the hair good cosmetic properties.

The compositions comprising at least one oxidation dye and a thickening system may be provided in the form of creams. The current technology in the oxidation dye field then requires that these compositions, in order to acquire a cream appearance, comprise high contents of fatty active agents such as alcohols, amides, and acids.

However, the present inventors have observed that as the viscosity of these creams change during their preservation or storage, it may be difficult to obtain a homogeneous mixture when these compositions are mixed in the form of a cream with an oxidizing agent. In addition, the consistency of these creams may make them difficult to use.

Advantageously and surprisingly, the present inventors have discovered that it was possible to obtain ready-to-use oxidation dyeing compositions which can exhibit at least one of the following properties: increased ease of mixing with at least one oxidizing agent and other optional components; improvement in the foaming properties; and increased ease of elimination, for example, during rinsing.

In addition, the compositions disclosed herein may not run and therefore remain well confined to the site of application; they may also make it possible to obtain intense and chromatic (radiant) shades with low selectivities and good fastness towards chemical agents (shampoo, permanent waving and the like) or natural agents (light, perspiration and the like) while offering the hair at least one good cosmetic property.

It has also been observed that the compositions disclosed herein can have reduced contents of fatty active agents compared with the contents of prior art compositions without the consistency of the composition (cream) being affected.

Disclosed herein is thus a composition for the oxidation dyeing of keratin fibers, for example, human keratin fibers, such as hair, comprising, in an appropriate dyeing medium, at least one oxidation dye, at least one fatty acid chosen from $C_{10}$–$C_{14}$ fatty acids and at least one cationic poly(vinyllactam) as described below.

Further disclosed herein is a ready-to-use composition for dyeing keratin fibers which comprises at least one oxidation dye, at least one fatty acid chosen from $C_{10}$–$C_{14}$ fatty acids and at least one cationic poly(vinyllactam) as defined herein and at least one oxidizing agent.

As defined herein, the expression "ready-to-use composition" is understood to mean a composition intended to be applied as it is to keratin fibers, that is to say that it can be stored as it is before use or a composition obtained from the fresh mixing of two or more compositions.

An effective quantity of the at least one cationic poly (vinyllactam) is thus introduced:
(i) into at least one composition A comprising the at least one oxidation dye and optionally at least one coupler, or
(ii) into at least one oxidizing composition B, or
(iii) into both at least one composition A and at least one composition B at the same time.

An effective quantity of the at least one fatty acid chosen from $C_{10}$–$C_{14}$ fatty acids is introduced:
(i) into at least one composition A comprising the at least one oxidation dye and optionally at least one coupler, or
(ii) into at least one oxidizing composition B, or
(iii) into both at least composition A and at least one composition B at the same time.

For example, the at least one fatty acid chosen from $C_{10}$–$C_{14}$ fatty acids may be in the composition comprising the at least one oxidation dye.

Further disclosed herein is a method for dyeing keratin fibers, for example, human keratin fibers, such as hair, comprising applying to the fibers at least one composition A comprising, in an appropriate dyeing medium, at least one oxidation dye, wherein the color is developed at alkaline, neutral or acidic pH with the aid of at least one composition B comprising at least one oxidizing agent which is mixed just at the time of use with the at least one composition A or which may be applied sequentially without intermediate rinsing, the at least one cationic poly(vinyllactam) as defined herein being present in the at least one composition A and/or in the at least one composition B and the at least one fatty acid chosen from $C_{10}$–$C_{14}$ fatty acids as defined herein being present in the at least one composition A and/or in the at least one composition B.

Further disclosed herein are multicompartment dyeing devices or "kits".

A two-compartment device disclosed herein comprises a first compartment comprising at least one composition A1 comprising, in an appropriate dyeing medium, at least one oxidation dye, and a second compartment comprising at least one composition B1 comprising, in an appropriate dyeing medium, at least one oxidizing agent, at least one cationic poly(vinyllactam) polymer as defined herein being present in the at least one composition A1 and/or in the at least one composition B1, and the at least one fatty acid chosen from $C_{10}$–$C_{14}$ fatty acids as defined herein being present in the at least one composition A1 and/or in the at least one composition B1.

Further disclosed herein is a three-compartment device comprising a first compartment comprising at least one composition A2 comprising, in an appropriate dyeing medium, at least one oxidation dye, a second compartment comprising at least one composition B2 comprising, in an appropriate dyeing medium, at least one oxidizing agent, and a third compartment comprising at least one composition C comprising, in an appropriate dyeing medium, at least one cationic poly(vinyllactam) polymer, it also being possible for the at least one composition A2 and/or the at least one composition B2 to comprise at least one cationic poly(vinyllactam) polymer as defined herein and it being also possible for the at least one composition A2 and/or the at least one composition B2 and/or the at least one composition C to comprise at least one fatty acid chosen from $C_{10}$–$C_{14}$ fatty acids as defined herein.

Other characteristics, aspects, subjects and advantages of the embodiments disclosed herein will appear more clearly on reading the description and the examples which follow, without, however, being limiting in nature.

Associative polymers are polymers whose molecules are capable, in the formulation medium, of combining with each other or with molecules of other compounds. Their chemical structure generally comprises at least one hydrophilic region and at least one hydrophobic region, wherein the at least one hydrophobic region comprises at least one fatty chain.

Cationic Poly(vinyllactam) Polymers

The at least one cationic poly(vinyllactam) polymer used in the compositions disclosed herein, comprises:
- at least one monomer (a) chosen from vinyllactam and alkylvinyllactam monomers and
- at least one monomer (b) chosen from monomers having the following structures (Ia) and (Ib):

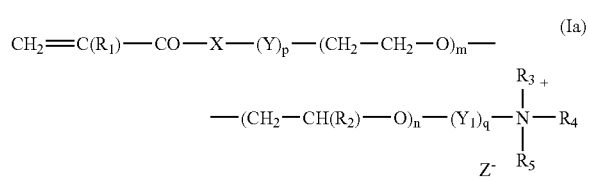

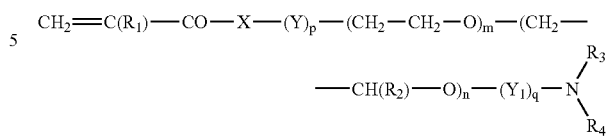

wherein:
X is chosen from an oxygen atom and radicals $NR_6$, $R_1$ and $R_6$, which may be identical or different, are each chosen from a hydrogen atom and linear and branched $C_1$–$C_5$ alkyl radicals, $R_2$ is chosen from linear and branched $C_1$–$C_4$ alkyl radicals, $R_3$, $R_4$ and $R_5$, which may be identical or different, are each chosen from a hydrogen atom, linear and branched $C_1$–$C_{30}$ alkyl radicals, and radicals of formula (II):

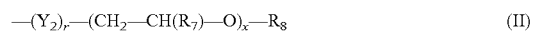

wherein: Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals, and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each integers equal to either the value zero, or the value 1, m and n, which may be identical or different, are each integers ranging from 0 to 100, x is an integer ranging from 1 to 100, and $Z^-$ is chosen from organic and inorganic acid anions, provided that:
at least one of the substituents $R_3$, $R_4$, $R_5$ or $R_8$ is chosen from linear and branched $C_9$–$C_{30}$ alkyl radicals, if m or n is different from zero, then q is equal to 1, and if m or n is equal to zero, then p or q is equal to 0.

The at least one cationic poly(vinyllactam) polymer used in the compositions disclosed herein may be crosslinked or noncrosslinked and may also be a block polymer.

The counterion $Z^-$ of the monomers of formula (Ia) may, for example, be chosen from halide ions, phosphate ions, a methosulphate ion, and a tosylate ion.

In at least one embodiment, $R_3$, $R_4$ and $R_5$, which may be identical or different, are each chosen from a hydrogen atom and linear and branched $C_1$–$C_{30}$ alkyl radicals.

In at least one embodiment, the at least one monomer (b) may be chosen from monomers of formula (Ia) wherein, for example, m and n are equal to zero.

The vinyllactam and alkylvinyllactam monomers may, for example, be chosen from compounds having the structure (III):

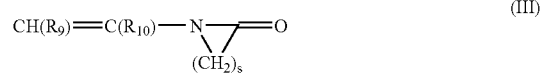

wherein:
s is an integer ranging from 3 to 6,
$R_9$ is chosen from a hydrogen atom and $C_1$–$C_5$ alkyl radicals, and
$R_{10}$ is chosen from a hydrogen atom and $C_1$–$C_5$ alkyl radicals,
provided that at least one of the radicals $R_9$ and $R_{10}$ is a hydrogen atom.

For example, the monomer (III) may be vinylpyrrolidone.

The at least one cationic poly(vinyllactam) polymer used in the compositions disclosed herein may also comprise at least one additional monomer. For example, the at least one additional monomer may be chosen from cationic and nonionic monomers.

For example, the compounds used in the compositions disclosed herein may be chosen from terpolymers comprising:
i) at least one monomer chosen from monomers of formula (III),
ii) at least one monomer chosen from monomers of formula (Ia) wherein p=1, q=0, $R_3$ and $R_4$, which may be identical or different, are each chosen from a hydrogen atom and $C_1$–$C_5$ alkyl radicals and $R_5$ is chosen from $C_9$–$C_{24}$ alkyl radicals, and
iii) at least one monomer chosen from monomers of formula (Ib) wherein $R_3$ and $R_4$, which may be identical or different, are each chosen from a hydrogen atom and $C_1$–$C_5$ alkyl radicals.

For example, the compositions disclosed herein may comprise terpolymers comprising, by weight, 40 to 95% of at least one monomer (i), 0.1 to 55% of at least one monomer (iii) and 0.25 to 50% of at least one monomer (ii).

Such polymers are described in International Patent Application No. WO-00/68282, the disclosure of which is hereby incorporated by reference.

The at least one cationic poly(vinyllactam) polymer used in the compositions disclosed herein may, for example, be chosen from the following terpolymers:
vinylpyrrolidone/dimethylaminopropylmethacrylamide/dodecyldimethylmethacrylamidopropylammonium tosylate,
vinylpyrrolidone/dimethylaminopropylmethacrylamide/cocoyldimethylmethacrylamidopropylammonium tosylate,
vinylpyrrolidone/dimethylaminopropylmethacrylamide/lauryldimethylmethacrylamidopropylammonium tosylate, and
vinylpyrrolidone/dimethylaminopropylmethacrylamide/lauryldimethylmethacrylamidopropylammonium chloride.

The weight-average molecular mass of the at least one cationic poly(vinyllactam) polymer disclosed herein may, for example, range from 500 to 20 000 000. Further, for example, the weight-average molecular mass may range from 200 000 to 2 000 000 and still further, for example, from 400 000 to 800 000.

In the at least one dyeing composition disclosed herein, the at least one cationic poly(vinyllactam) described herein may, for example, be used in a quantity which ranges from 0.01 to 10% by weight, relative to the total weight of the composition, further, for example, this quantity can range from 0.1 to 5% by weight, relative to the total weight of the composition.

For example, the viscosity of the compositions disclosed herein is greater than 1 000 cp, measured at 25° C. using a RHEOMAT RM 180 rheometer at a shear rate of 200 s$^{-1}$.

$C_{10}$–$C_{14}$ Fatty Acids

The at least one fatty acid used in the composition disclosed herein are chosen from $C_{10}$–$C_{14}$ fatty acids.

The $C_{10}$–$C_{14}$ fatty acids may, for example, be chosen from at least one of capric, lauric and myristic acids.

Lauric acid may be used in the compositions disclosed herein, for example.

The $C_{10}$–$C_{14}$ fatty acids may be free, partially or completely neutralized in the compositions disclosed herein. For example, the $C_{10}$–$C_{14}$ fatty acids may be completely neutralized.

In the at least one dyeing composition disclosed herein, the at least one fatty acid chosen from $C_{10}$–$C_{14}$ fatty acids may, for example, be present in a quantity ranging from 0.1 % to 40% by weight, relative to the total weight of the composition. Further, for example, this quantity can range from 2% to 25% by weight, relative to the total weight of the composition, and further, for example, from 5% to 20% by weight, relative to the total weight of the composition.

Oxidation Dyes

The at least one oxidation dye which can be used in the compositions disclosed herein may, for example, be chosen from oxidation bases and couplers.

For example, the compositions disclosed herein may comprise at least one oxidation base.

The at least one oxidation base which can be used in the compositions disclosed herein may, for example, be chosen from those conventionally known in oxidation dyeing. For example, the at least one oxidation base may be chosen from para-phenylenediamines, double bases, ortho- and para-aminophenols, the following heterocyclic bases and the acid addition salts thereof.

For example, the at least one oxidation base may be chosen from the following:
(A) the para-phenylenediamines of the following formula (IV) and the acid addition salts thereof:

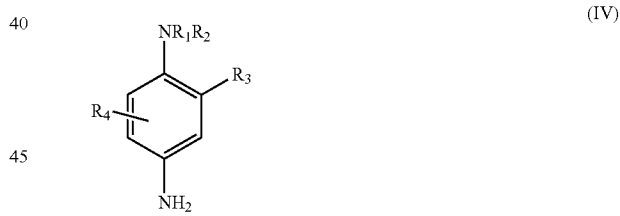

wherein:
$R_1$ is chosen from a hydrogen atom, $C_1$–$C_4$ alkyl radicals, monohydroxy($C_1$–$C_4$ alkyl) radicals, polyhydroxy($C_2$–$C_4$ alkyl) radicals, ($C_1$–$C_4$)alkoxy($C_1$–$C_4$)alkyl radicals, $C_1$–$C_4$ alkyl radicals substituted with at least one nitrogen-containing group, phenyl radicals and a 4'-aminophenyl radical;
$R_2$ is chosen from a hydrogen atom, $C_1$–$C_4$ alkyl radicals, monohydroxy($C_1$–$C_4$ alkyl) radicals, polyhydroxy($C_2$–$C_4$ alkyl) radicals, ($C_1$–$C_4$)alkoxy($C_1$–$C_4$)alkyl radicals and $C_1$–$C_4$ alkyl radicals substituted with at least one nitrogen-containing group;
$R_1$ and $R_2$ may also form, with the nitrogen atom to which they are attached, at least one heterocycle chosen from 5- and 6-membered nitrogen-containing heterocycles optionally substituted with at least one group chosen from alkyl, hydroxyl and ureido groups;
$R_3$ is chosen from a hydrogen atom, halogen atoms such as a chlorine atom, $C_1$–$C_4$ alkyl radicals, a sulpho radical, a carboxyl radical, monohydroxy(C$_1$–C$_4$ alkyl) radicals, hydroxy(C$_1$–C$_4$ alkoxy) radicals, acetylamino(C$_1$–C$_4$ alkoxy) radicals, mesylamino(C$_1$–C$_4$ alkoxy) radicals, and carbamoylamino(C$_1$–C$_4$ alkoxy) radicals, and R$_4$ is chosen from a hydrogen atom, halogen atoms, and C$_1$–C$_4$ alkyl radicals.

The nitrogen-containing groups of formula (IV) above may, for example, be chosen from amino, mono(C$_1$–C$_4$) alkylamino, (C$_1$–C$_4$)dialkylamino, (C$_1$–C$_4$)trialkylamino, monohydroxy(C$_1$–C$_4$)alkylamino, imidazolinium and ammonium radicals.

The para-phenylenediamines of formula (IV) above may, for example, be chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylened iamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and the acid addition salts thereof.

The para-phenylenediamines of formula (IV) above may, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and the acid addition salts thereof.

(B) As defined herein, "double bases" is understood to mean compounds comprising at least two aromatic rings on which at least one group chosen from amino and hydroxyl groups is attached.

The double bases which can be used as the at least one oxidation base in the dyeing compositions disclosed herein may, for example, be chosen from compounds corresponding to the following formula (V), and the acid addition salts thereof:

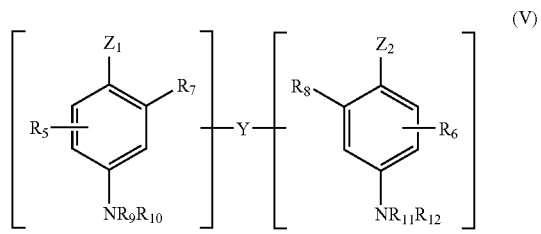

wherein:

Z$_1$ and Z$_2$, which may be identical or different, are each chosen from hydroxyl and —NH$_2$ radicals which may be substituted at least one entity chosen from C$_1$–C$_4$ alkyl radicals and linking arm Y;

the linking arm Y is chosen from linear and branched alkylene chains comprising from 1 to 14 carbon atoms, which may be interrupted by or which may end with at least one entity chosen from nitrogen-comprising groups and heteroatoms such as oxygen, sulphur and nitrogen atoms, and the linking arm Y may be optionally substituted with at least one radical chosen from hydroxyl and C$_1$–C$_6$ alkoxy radicals;

R$_5$ and R$_6$, which may be identical or different, are each chosen from a hydrogen atom, halogen atoms, C$_1$–C$_4$ alkyl radicals, monohydroxy(C$_1$–C$_4$ alkyl) radicals, polyhydroxy(C$_2$–C$_4$ alkyl) radicals, amino(C$_1$–C$_4$ alkyl) radicals, and the linking arm Y; and R$_7$, R$_8$, R$_9$, R$_{10}$, R$_{11}$ and R$_{12}$, which may be identical or different, are each chosen from a hydrogen atom, the linking arm Y and C$_1$–C$_4$ alkyl radicals;

it being understood that the compounds of formula (V) comprise only one linking arm Y per molecule.

The nitrogen-containing groups of formula (V) above may, for example, be chosen from amino, mono(C$_1$–C$_4$) alkylamino, (C$_1$–C$_4$)dialkylamino, (C$_1$–C$_4$)trialkylamino, monohydroxy(C$_1$–C$_4$)alkylamino, imidazolinium and ammonium radicals.

The double bases of formulae (V) above may, for example, be chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis-(ethyl-N,N'-bis(4'-amino-3'-methylphenyl)ethylenediamine, 1,8-bis(2,5-diaminophenoxy)-3,6-dioxaoctane, and the acid addition salts thereof.

The double bases of formula (V) may, for example, be chosen from N,N'-bis-(β-hydroxyethyl)-N,N'-bis(4'-aminophenyl)-1,3-diaminopropanol, 1,8-bis(2,5-diaminophenoxy)-3,6-dioxaoctane and the acid addition salts thereof.

(C) para-aminophenols corresponding to the following formula (VI), and the acid addition salts thereof:

wherein:

R$_{13}$ is chosen from a hydrogen atom, halogen atoms such as fluorine, C$_1$–C$_4$ alkyl, monohydroxy(C$_1$–C$_4$ alkyl), (C$_1$–C$_4$)alkoxy(C$_1$–C$_4$)alkyl, amino (C$_1$–C$_4$ alkyl), and hydroxy(C$_1$–C$_4$)alkylamino(C$_1$–C$_4$ alkyl) radicals, and R$_{14}$ is chosen from a hydrogen atom, halogen atoms such as fluorine, C$_1$–C$_4$ alkyl, monohydroxy(C$_1$–C$_4$ alkyl), polyhydroxy(C$_2$–C$_4$ alkyl), amino(C$_1$–C$_4$ alkyl), cyano (C$_{-C4}$ alkyl) and (C$_1$–C$_4$)alkoxy(C$_1$–C$_4$)alkyl radicals.

The para-aminophenols of formula (VI) above may, for example, be chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and the acid addition salts thereof.

(D) the ortho-aminophenols which can be used as oxidation bases in the compositions disclosed herein may, for example, be chosen from 2-aminophenol, 2-amino-1-hydroxy-5-methylbenzene, 2-amino-1-hydroxy-6-methylbenzene, 5-acetamido-2-aminophenol, and the acid addition salts thereof.

(E) the heterocyclic bases which can be used as oxidation bases in the dyeing compositions disclosed herein, may, for example, be chosen from pyridine derivatives, pyrimidine derivatives, pyrazole derivatives, and acid addition salts thereof.

The pyridine derivatives may, for example, be chosen from the compounds described for example in Patent Nos. GB 1,026,978 and GB 1,153,196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine, and the acid addition salts thereof.

The pyrimidine derivatives may, for example, be chosen from the compounds described for example in German Patent No. DE 2,359,399 and Japanese Patent Nos. JP 88-169,571 and JP 91-10659 and International Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application No. FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; and 3-amino-5-methyl-7-imidazolylpropylaminopyrazolo[1,5-a]pyrimidine; and the acid addition salts thereof and tautomeric forms thereof, when a tautomeric equilibrium exists.

The pyrazole derivatives may, for example, be chosen from the compounds described in Patent Nos. DE 3,843,892, DE 4,133,957 and Patent Application Nos. WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methyl pyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the acid addition salts thereof.

The at least one oxidation base may, for example, be present in an amount ranging from 0.0005 to 20% by weight, relative to the total weight of the composition and further, for example, from 0.005 to 8% by weight, relative to the total weight of the composition.

The at least one coupler which can be used in the dyeing method disclosed herein may, for example, be chosen from those conventionally used in oxidation dyeing compositions. For example, the at least one coupler may be chosen from meta-aminophenols, meta-phenylenediamines, meta-diphenols, naphthols and heterocyclic couplers such as indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines and the acid addition salts thereof.

The at least one coupler may, for example, be chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole and the acid addition salts thereof.

The at least one coupler may be present in an amount ranging, for example, from 0.0001 to 20% by weight, relative to the total weight of the composition, and further, for example, in an amount ranging from 0.005 to 5% by weight, relative to the total weight of the composition.

In general, the acid addition salts of the at least one oxidation base and the at least one coupler may, for example, be chosen from hydrochlorides, hydrobromides, sulfates and tartrates, lactates and acetates.

The compositions disclosed herein may further comprise, in addition to the at least one oxidation dye defined above, at least one direct dye in order to enrich the shades with glints. The at least one direct dyes may, for example, be chosen from neutral, cationic and anionic nitro, azo and anthraquinone dyes in an amount ranging from 0.001 to 20% by weight, relative to the total weight of the composition, further, for example, from 0.01 to 10% by weight, relative to the total weight of the composition.

The at least one composition A and/or the at least one composition B and/or the at least one composition C may in addition comprise, for example, at least one additional polymer chosen from at least one amphoteric polymer and at least one additional cationic polymer different from the cationic poly(vinyllactams) disclosed herein.

Additional Cationic Polymers

As defined herein, the expression "cationic polymer" means any polymer comprising at least one group chosen from cationic groups and groups which can be ionized to cationic groups.

The at least one additional cationic polymer which can be used in the compositions disclosed herein may, for example, be chosen from those polymers already known per se to improve the cosmetic properties of hair, for example, those described in Patent Application No. EP-A-337 354 and in French Patent Nos. FR-2,270,846, 2,383,660, 2,598,611, 2,470,596 and 2,519,863.

The at least one additional cationic polymer may, for example, be chosen from those polymers comprising units comprising at least one group chosen from primary, secondary, tertiary and quaternary amino groups which may either form part of the principal polymeric chain, or which may be carried by a side substituent directly linked thereto.

The at least one additional cationic polymer used may have a number-average molecular mass ranging, for example, from 500 to $5 \times 10^6$ and further, for example, from $10^3$ to $3 \times 10^6$.

The at least one additional cationic polymer may, for example, be chosen from polyamine, polyamino amide and quaternary polyammonium type polymers.

These are known products, described, for example, in French Patent Nos. 2,505,348 and 2,542,997. These polymers may, for example, be chosen from:

(1) the homopolymers or copolymers derived from acrylic or methacrylic esters or amides and comprising at least one of the units of the following formulae (VII), (VIII), (IX) and (X):

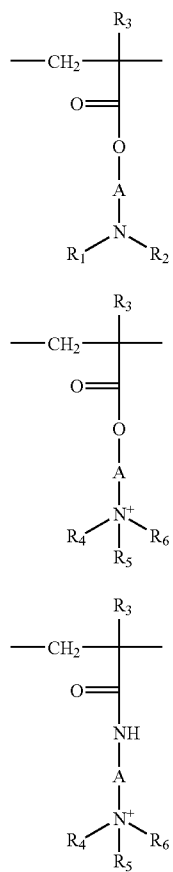

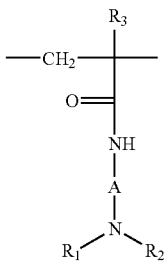

wherein:

$R_3$, which may be identical or different, are each chosen from a hydrogen atom and a $CH_3$ radical;

A, which may be identical or different, is chosen from linear and branched alkyl groups comprising from 1 to 6 carbon atoms, for example, 2 or 3 carbon atoms, and hydroxyalkyl groups comprising from 1 to 4 carbon atoms;

$R_4$, $R_5$, $R_6$, which may be identical or different, are each chosen from alkyl groups comprising from 1 to 18 carbon atoms, for example, alkyl groups comprising from 1 to 6 carbon atoms, and a benzyl radical;

$R_1$ and $R_2$, which may be identical or different, are each chosen from a hydrogen atom and alkyl groups comprising from 1 to 6 carbon atoms such as a methyl or an ethyl group;

the charged species of formula (VIII) and (IX) are combined with a counterion $X^-$, which is chosen from anions derived from inorganic and organic acids such as a methosulphate anion or a halide such as chloride or bromide.

The polymers of the family (1) may comprise, in addition, at least one unit derived from comonomers which may be chosen from the family of acrylamides, methacrylamides, diacetone acrylamides, acrylamides and methacrylamides substituted on the nitrogen with at least one group chosen from lower ($C_1$–$C_4$)alkyls, acrylic and methacrylic acids and esters thereof, vinyllactams such as vinylpyrrolidone and vinylcaprolactam, and vinyl esters.

Thus, the polymers of family (1) may, for example, be chosen from:

copolymers of acrylamide and dimethylamino-ethyl methacrylate quaternized with dimethyl sulphate or with a dimethyl halide such as the polymers sold under the name HERCOFLOC® by the company HERCULES, the copolymers of acrylamide and methacryloyloxy-ethyltrimethylammonium chloride described, for example, in Patent Application No. EP-A-080976 and sold under the name BINA QUAT P 100® by the company CIBA GEIGY, the copolymer of acrylamide and methacryloyloxy-ethyltrimethylammonium methosulphate sold under the name RETEN® by the company HERCULES, the vinylpyrrolidone/dialkylaminoalkyl acrylate and methacrylate copolymers, optionally quaternized, such as the products sold under the name "GAFQUAT®" by the company ISP such as for example "GAFQUAT 734" and "GAFQUAT 755" or alternatively the products called "COPOLYMER 845®, 958® and 937®". These polymers are described in detail in French Patent Nos. 2,077,143 and 2,393,573, the dimethylaminoethyl methacrylate/vinylcapro-lactam/vinylpyrrolidone terpolymers such as the product sold under the name GAFFIX VC 713® by the company ISP, the vinylpyrrolidone/methacrylamidopropyldimethyl-amine copolymers marketed, for example, under the name STYLEZE CC 10® by ISP, and the quaternized vinylpyrrolidone/dimethyl-aminopropyl methacrylamide copolymers such as the product sold under the name "GAFQUAT® HS 100" by the company ISP.

(2) The cellulose ether derivatives comprising at least one quaternary ammonium group, described in French Patent No. 1,492,597, for example, the polymers marketed under the names "JR®" (JR 400, JR 125, JR 30M) and "LR®" (LR 400, LR 30M) by the company Union Carbide Corporation. These polymers are also defined in the CTFA dictionary as hydroxyethyl cellulose quaternary ammoniums which have reacted with an epoxide substituted by at least one trimethylammonium group.

(3) Cationic cellulose derivatives such as cellulose copolymers and cellulose derivatives grafted with at least one quaternary ammonium water-soluble monomer, and described, for example, in U.S. Pat. No. 4,131,576, such as hydroxyalkyl celluloses like hydroxymethyl, hydroxyethyl and hydroxypropyl celluloses grafted, for example, with at least one salt chosen from methacryloylethyltrimethylammonium, methacrylamidopropyltrimethylammonium and dimethyldiallylammonium salts.

The commercialized products corresponding to this definition are, for example, the products sold under the name "Celquat® L 200" and "Celquat® H 100" by the company National Starch.

(4) The cationic polysaccharides described, for example, in U.S. Pat. Nos. 3,589,578 and 4,031,307 such as guar gums comprising at least one cationic trialkylammonium group. Guar gums modified with a 2,3-epoxypropyltrimethylammonium salt (e.g. chloride) may for example be used.

Such products are marketed, for example, under the trade names JAGUAR® C13 S, JAGUAR® C 15, JAGUAR® C 17 or JAGUAR® C 162 by the company MEYHALL.

(5) Polymers comprising at least one piperazinyl unit and at least one divalent radical chosen from alkylene and hydroxyalkylene divalent radicals comprising at least one chain chosen from straight and branched chains, optionally interrupted by at least one entity chosen from oxygen, sulphur and nitrogen atoms and aromatic and heterocyclic rings, as well as the oxidation and/or quaternization products of these polymers. Such polymers are described, for example, in French Patent Nos. 2,162,025 and 2,280,361.

(6) Water-soluble polyaminoamides prepared, for example, by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or with an oligomer resulting from the reaction of a difunctional compound which is reactive towards a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include at least one tertiary amine functional group, quaternized. Such polymers are described, for example, in French Patent Nos. 2,252,840 and 2,368,508.

(7) Polyaminoamide derivatives resulting from the condensation of polyalkylenepolyamines with polycarboxylic acids, followed by an alkylation with at least one difunctional agent. The polyaminoamide derivatives may, for example, be chosen from adipic acid—dialkylaminohydroxyalkyldialkylenetriamine polymers wherein the alkyl radical comprises from 1 to 4 carbon atoms, for example, a methyl, ethyl or propyl group. Such polymers are described, for example, in French Patent No. 1,583,363.

These derivatives may, for example, be chosen from the adipic acid/dimethylaminohydroxypropyl/diethylenetriamine polymers sold under the name "Cartaretine® F, F4 or F8" by the company Sandoz.

(8) Polymers obtained by reaction of a polyalkylenepolyamine comprising two primary amine groups and at least one secondary amine group with a dicarboxylic acid chosen from diglycolic acid and saturated aliphatic dicarboxylic acids comprising from 3 to 8 carbon atoms. The molar ratio of the polyalkylenepolyamine to the dicarboxylic acid ranges from 0.8:1 to 1.4:1; the polyaminoamide resulting therefrom being made to react with epichlorohydrin in a molar ratio of epichlorohydrin relative to the secondary amine group of the polyaminoamide ranging from 0.5:1 to 1.8:1. Such polymers are described, for example, in U.S. Pat. Nos. 3,227,615 and 2,961,347.

Polymers of this type are marketed, for example, under the name "Hercosett® 57" by the company Hercules Inc. or under the name of "PD 170®" or "Delsette 101®" by the company Hercules in the case of the copolymer of adipic acid/epoxypropyl/diethylene-triamine.

(9) Cyclopolymers of alkyldiallylamine and of dialkyldiallylammonium, such as the homopolymers and copolymers comprising, as main constituent of the chain, units corresponding to the formulae (XI) and (XII):

$$\text{---}(CH_2)_t\text{---}CR_9 \underset{\underset{R_7}{\overset{H_2C}{\diagdown}}\underset{R_8}{\overset{N^+}{\diagup}}\underset{}{\diagdown}}{\overset{(CH_2)_k}{\diagup}} \overset{}{\underset{}{\diagdown}} C(R_9)\text{---}CH_2\text{---} \quad Y^- \tag{XI}$$

$$\text{---}(CH_2)_t\text{---}CR_9 \underset{\underset{R_7}{\overset{H_2C}{\diagdown}}\underset{}{\overset{N}{\diagup}}\underset{}{\diagdown}}{\overset{(CH_2)_k}{\diagup}} \overset{}{\underset{}{\diagdown}} C(R_9)\text{---}CH_2\text{---} \tag{XII}$$

wherein k and t are equal to 0 or 1, the sum k+t being equal to 1; $R_9$ is chosen from a hydrogen atom and a methyl radical; $R_7$ and $R_8$, which may be identical or different, are chosen from alkyl groups comprising from 1 to 8 carbon atoms, hydroxyalkyl groups wherein the alkyl group comprises 1 to 5 carbon atoms, and lower ($C_1$–$C_4$)amidoalkyl groups or $R_7$ and $R_8$ may form, together with the nitrogen atom to which they are attached, at least one heterocyclic group such as piperidinyl or morpholinyl; $R_7$ and $R_8$, which may be identical or different, are each chosen from alkyl groups comprising from 1 to 4 carbon atoms; $Y^-$ is chosen from anions such as bromide, chloride, acetate, borate, citrate, tartrate, bisulphate, bisulphite, sulphate and phosphate. These polymers are described, for example, in French Patent No. 2,080,759 and in its Certificate of Addition 2,190,406.

The polymers defined above may, for example, be chosen from dimethyldiallylammonium chloride homopolymer sold under the name "Merquat® 100" by the company Calgon (and its homologues of low weight-average molecular masses) and the copolymers of diallyl-dimethylammonium chloride and acrylamide marketed under the name "MERQUAT® 550".

(10) The quaternary diammonium polymer comprising repeating units corresponding to the formula:

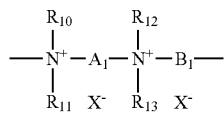

(XIII)

wherein:

$R_{10}$, $R_{11}$, $R_{12}$ and $R_{13}$, which may be identical or different, are each chosen from aliphatic, alicyclic and arylaliphatic radicals comprising from 1 to 20 carbon atoms and lower hydroxyalkyl aliphatic radicals, or $R_{10}$, $R_{11}$, $R_{12}$ and $R_{13}$, together or separately, form, with the nitrogen atoms to which they are attached, at least one heterocyclic ring optionally comprising a second heteroatom other than nitrogen, or $R_{10}$, $R_{11}$, $R_{12}$ and $R_{13}$, which may be identical or different, are each chosen from linear and branched $C_1$–$C_6$ alkyl radicals substituted with at least one group chosen from nitrile, ester, acyl, amide, —CO—O—$R_{14}$—D and —CO—NH—$R_{14}$—D groups wherein $R_{14}$ is chosen from alkylene groups and D is chosen from quaternary ammonium groups;

$A_1$ and $B_1$, which may be identical or different, are each chosen from polymethylene groups comprising from 2 to 20 carbon atoms which may be linear or branched, saturated or unsaturated and which may comprise, bonded to or inserted into the main chain, at least one entity chosen from aromatic rings, oxygen and sulphur atoms, sulphoxide, sulphone, disulphide, amino, alkylamino, hydroxyl, quaternary ammonium, ureido, amide and ester groups, and $X^-$ is chosen from anions derived from inorganic and organic acids;

A1, $R_{10}$ and $R_{12}$ may form, together with the two nitrogen atoms to which they are attached, a piperazine ring; in addition if A1 is chosen from saturated and unsaturated, linear and branched alkylene and hydroxyalkylene radicals, B1 may also be chosen from groups —$(CH_2)_n$—CO—D—OC—$(CH_2)_n$— wherein n is a number ranging from 1 to 100, for example, from 1 to 50, and D is chosen from:

a) a glycol residue of formula: —O—Z—O—, wherein Z is chosen from linear and branched hydrocarbon radicals and groups corresponding to one of the following formulae:

—$(CH_2$—$CH_2$—$O)_x$—$CH_2$—$CH_2$—

—$[CH_2$—$CH(CH_3)$—$O]_y$—$CH_2$—$CH(CH_3)$— wherein x and y is an integer ranging from 1 to 4, representing a defined and unique degree of polymerization or any number ranging from 1 to 4 representing a mean degree of polymerization;

b) a disecondary diamine residue such as a piperazine derivative;

c) a diprimary diamine residue of formula: —NH—Y—NH—, wherein Y is chosen from linear and branched hydrocarbon radicals and the divalent radical —$CH_2$—$CH_2$—S—S—$CH_2$—$CH_2$—; and d) a ureylene group of formula: —NH—CO—NH—;

$X^-$ is, for example, chosen from anions such as chloride or bromide.

These polymers have a number-average molecular mass ranging, for example, from 1000 to 100 000.

Polymers of this type are described, for example, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use, for example, the polymers comprising repeating units corresponding to the following formula (XIV):

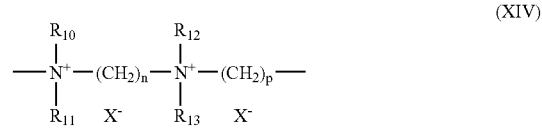

(XIV)

wherein:

$R_{10}$, $R_{11}$, $R_{12}$ and $R_{13}$, which may be identical or different, are chosen from alkyl and hydroxyalkyl radicals comprising from 1 to 4 carbon atoms, n and p are integers ranging from 2 to 20, and $X^-$ is chosen from anions derived from inorganic and organic acids.

(11) The quaternary polyammonium polymers comprising recurring units of formula (XV):

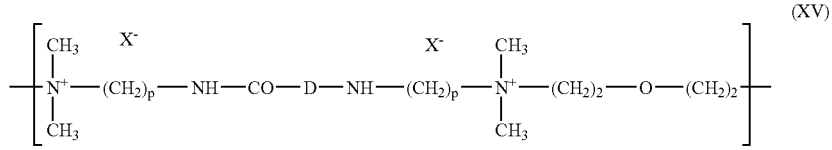

(XV)

wherein:

p is an integer ranging from 1 to 6,

D may be zero or may be chosen from groups —$(CH_2)_r$—CO— wherein r is a number equal to 4 or to 7, and $X^-$ is chosen from anions.

Such polymers may be prepared according to the methods described in U.S. Pat. Nos. 4,157,388, 4,702,906, 4,719,282. These polymers are, for example, described in Patent Application No. EP-A-122 324.

Among these polymers, there may be mentioned, for example, the products "Mirapol® A 15", "Mirapol® AD1", "Mirapol® AZ1" and "Mirapol® 175" sold by the company Miranol.

(12) Quaternary vinylpyrrolidone and vinylimidazole polymers such as, the products marketed under the names Luviquat® FC 905, FC 550 and FC 370 by the company B.A.S.F.
(13) Polyamines like the Polyquart H sold by Henkel, referenced under the name of "Polyethylene Glycol (15) Tallow Polyamine" in the CTFA dictionary.
(14) The crosslinked polymers of methacryloyloxy($C_1$–$C_4$ alkyl)tri($C_1$–$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. For example, it is possible to employ a crosslinked acrylamide/methacryloyloxyethyltrimethylammonium chloride copolymer (20/80 by weight) in the form of a dispersion comprising 50% by weight of said copolymer in mineral oil. This dispersion is marketed under the name of "SALCARE® SC 92" by the company ALLIED COLLOIDS. It is also possible to employ a crosslinked methacryloyloxyethyltri-methylammonium chloride homopolymer comprising approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be used in compositions disclosed herein may, for example, be chosen from polyalkyleneimines, such as, polyethyleneimines, polymers comprising vinylpyridine and vinylpyridinium units, condensates of polyamines and of epichlorohydrin, quaternary polyureylenes and chitin derivatives.

Among all the cationic polymers which may be used in the compositions disclosed herein, the polymers of families (1), (9), (10), (11) and (14) and, for example, the polymers with the recurring units of the following formulae (W) and (U) may be used:

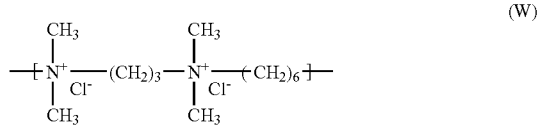

(W)

and, for example, those polymers whose molecular weight, determined by gel permeation chromatography, ranges from 9500 to 9900;

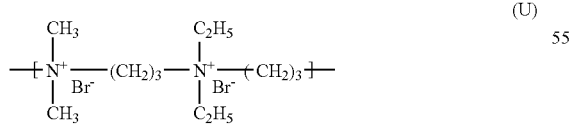

(U)

and, for example, those polymers whose molecular weight, determined by gel permeation chromatography, is about 1200.

The at least one additional cationic polymer in the composition disclosed herein may range, for example, from 0.01 to 10% by weight, relative to the total weight of the composition, further, for example, from 0.05 to 5% by weight, relative to the total weight of the composition, and further, for example, from 0.1 to 3% by weight, relative to the total weight of the composition.

Amphoteric Polymers

The at least one amphoteric polymer which can be used in the compositions disclosed herein may be chosen from the polymers comprising units K and M distributed statistically in the polymer chain wherein K is a unit derived from a monomer comprising at least one basic nitrogen atom and M is a unit which is derived from an acidic monomer comprising at least one group chosen from carboxylic and sulphonic groups or alternatively K and M may be chosen from groups which are derived from zwitterionic monomers of carboxybetaines and of sulphobetaines;

K and M may also be chosen from cationic polymer chains comprising at least one group chosen from primary, secondary, tertiary and quaternary amine groups, wherein at least one of the amine groups bears a carboxylic or sulphonic group linked via a hydrocarbon radical or alternatively K and M form part of a chain of a polymer with an α,β-dicarboxylic ethylene unit in which one of the carboxylic groups has been caused to react with a polyamine comprising at least one amine chosen from primary and secondary amine groups.

The at least one amphoteric polymers corresponding to the definition given above, for example, may be chosen from the following polymers:

1) The polymers resulting from the copolymerization of at least one monomer derived from a vinyl compound bearing at least one carboxylic group such as acrylic acid, methacrylic acid, maleic acid, alpha-chloroacrylic acid, and at least one basic monomer derived from a substituted vinyl compound comprising at least one basic atom such as dialkylaminoalkyl methacrylate and acrylate, dialkylaminoalkylmethacrylamide and acrylamide. Such compounds are described, for example, in U.S. Pat. No. 3,836,537. Mention may also be made of the sodium acrylate/acryamidopropyltrimethylammonium chloride copolymer sold under the name POLYQUART KE® 3033 by the company HENKEL.

The vinyl compound may also be a dialkyldiallylammonium salt such as dimethyldiallylammonium chloride. The copolymers of acrylic and of the latter monomer are sold under the names MERQUAT® 280, MERQUAT® 295 and MERQUAT® PLUS 3330 by the company CALGON.

(2) The polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising at least one substituent chosen from primary, secondary, tertiary and quaternary amine substituents of acrylic and methacrylic acids and the product of quaternization of dimethyl-aminoethyl methacrylate with dimethyl or diethyl sulphate.

The N-substituted acrylamides or methacrylamides used in the compositions disclosed herein are groups, for example, wherein the alkyl radicals comprise from 2 to 12 carbon atoms such as N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen, for example, from acrylic, methacrylic, crotonic, itaconic, maleic and fumaric acids as well as the alkyl monoesters comprising from 1 to 4 carbon atoms of maleic or fumaric anhydrides or acids.

The basic comonomers may, for example, be chosen from methacrylates of aminoethyl, butylaminoethyl, N,N'-dimethylaminoethyl, and N-tert-butylaminoethyl.

The copolymers whose CTFA name (4th ed. 1991) is octylacrylamide/acrylates/butylaminoethylmethacrylate copolymer such as the products sold under the name AMPHOMER® or LOVOCRYL® 47 by the company NATIONAL STARCH can, for example, be used in the compositions disclosed herein.

(3) partially or completely alkylated and crosslinked polyaminoamides derived from polyaminoamides of general formula:

(XVI)

wherein $R_{19}$ is chosen from a divalent radical derived from saturated dicarboxylic acid, mono- and dicarboxylic aliphatic acids comprising an ethylenic double bond, esters of a lower alkanol comprising from 1 to 6 carbon atoms of these acids or a radical derived from the addition of any one of the acids to amines chosen from bis-primary and bis-secondary amine, and Z is chosen from bis-primary, mono- and bis-secondary polyalkylene-polyamine radicals and, for example, Z represents:

a) in proportions ranging from 60 to 100 mol %, the radical

(XVII)

wherein x=2 and p=2 or 3, or alternatively x=3 and p=2 this radical being derived from diethylenetriamine, triethylenetetraamine or dipropylenetriamine;

b) in proportions ranging from 0 to 40 mol %, the radical (XVII) above, wherein x=2 and p=1 and which is derived from ethylenediamine, or the radical which is derived from piperazine:

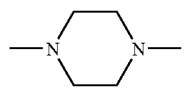

c) in proportions ranging from 0 to 20 mol %, the radical —NH—$(CH_2)_6$—NH— which is derived from hexamethylenediamine, these polyaminoamines can be crosslinked by adding at least one bifunctional crosslinking agent chosen from the epihalohydrins, diepoxides, dianhydrides, bis-unsaturated derivatives, using from 0.025 to 0.35 mol of crosslinking agent per amine group of the polyaminoamide and alkylated by the action of acrylic acid, chloroacetic acid or of an alkanesultone or salts thereof.

The saturated carboxylic acids may, for example, be chosen from acids comprising from 6 to 10 carbon atoms such as adipic acid, 2,2,4-trimethyladipic acid, 2,4,4-trimethyladipic acid, terephthalic acid, and acids comprising an ethylene double bond such as acrylic acid, methacrylic acid and itaconic acid.

The alkanesultones used in the alkylation may, for example, be chosen from propane sultone and butane sultone, and the salts of the alkylating agents can, for example, be chosen from sodium and potassium salts.

4) polymers comprising zwitterionic units of formula:

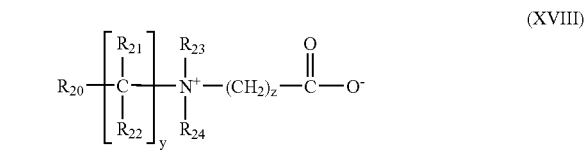

(XVIII)

wherein:
$R_{20}$ is chosen from polymerizable unsaturated groups such as an acrylate, methacrylate, acrylamide and methacrylamide groups,
y and z, which may be identical or different, are each integers ranging from 1 to 3,
$R_{21}$ and $R_{22}$, which may be identical or different, are each chosen from a hydrogen atom, a methyl group, an ethyl group and a propyl group, and
$R_{23}$ and $R_{24}$, which may be identical or different, are each chosen from a hydrogen atom and alkyl radicals such that the sum of the carbon atoms in $R_{23}$ and $R_{24}$ does not exceed 10.

The polymers comprising such units may also comprise units derived from non-zwitterionic monomers such as monomers chosen from dimethyl, diethylaminoethyl acrylates and methacrylates and alkyl acrylates, methacrylates, acrylamides, methacrylamides and vinyl acetate.

The copolymer of butyl methacrylate/dimethylcarboxymethylammonioethyl methacrylate such as the product sold under the name DIAFORMER Z301® by the company SANDOZ may also, for example, be used in the compositions disclosed herein.

(5) polymers derived from chitosan comprising monomeric units corresponding to the following formulae (XIX), (XX), (XXI):

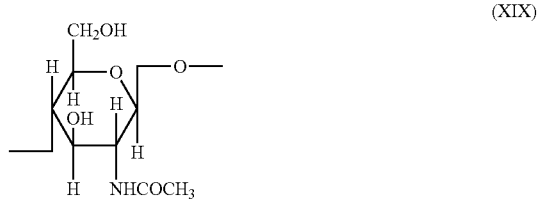

(XIX)

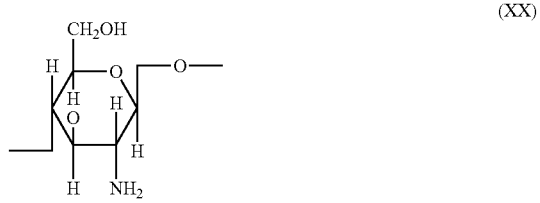

(XX)

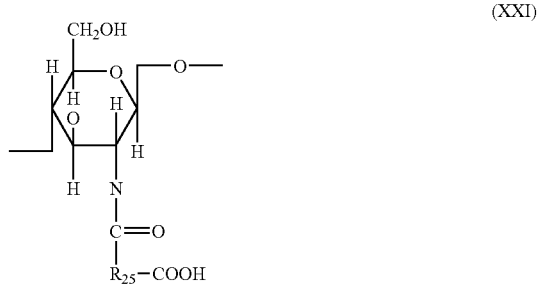

(XXI)

the (XIX) unit being present in proportions ranging from 0 to 30%, the (XX) unit in proportions ranging from 5 to 50% and the (XXI) unit in proportions ranging from 30 to 90%, it being understood that in the (XXI) unit, $R_{25}$ is chosen from radicals of formula:

$$R_{26}-\underset{\underset{R_{27}}{|}}{C}-(O)_q-\underset{\underset{R_{28}}{|}}{C}-H$$

wherein q is equal to zero or 1;

if q=0, $R_{26}$, $R_{27}$ and $R_{28}$, which may be identical or different, are each chosen from a hydrogen atom, methyl, hydroxyl, acetoxy and amino residues, monoalkylamine residues and dialkylamine residues which are optionally interrupted by at least one nitrogen atom and/or optionally substituted with at least one group chosen from amine, hydroxyl, carboxyl, alkylthio and sulphonic groups, and alkylthio residues wherein the alkyl group bears an amino residue, at least one of the $R_{26}$, $R_{27}$ and $R_{28}$ radicals being, in this case, a hydrogen atom;

or if q=1, $R_{26}$, $R_{27}$ and $R_{28}$, which may be identical or different, are each chosen from a hydrogen atom and the salts formed by these compounds with bases or acids.

(6) The polymers derived from the N-carboxyalkylation of chitosan such as N-carboxymethyl chitosan and N-carboxybutyl chitosan sold under the name "EVALSAN®" by the company JAN DEKKER.

(7) The polymers corresponding to the general formula (XXII) as described for example in French Patent No. 1,400,366:

$$\left[-(\underset{\underset{R_{29}}{|}}{CH}-CH_2)-\left[\underset{\underset{\underset{\underset{\underset{\underset{R_{31}}{|}}{N-R_{32}}}{|}}{R_{33}}}{N-R_{30}}}{\overset{\overset{}{|}}{COOH\ CO}}\right]\right]_r$$ (XXII)

wherein:

$R_{29}$ is chosen from a hydrogen atom, a $CH_3O$, $CH_3CH_2O$ radical, and a phenyl radical, $R_{30}$ is chosen from a hydrogen atom and lower alkyl radicals such as methyl and ethyl radicals, $R_{31}$ is chosen from a hydrogen atom and lower alkyl radicals such as methyl and ethyl radicals, $R_{32}$ is chosen from lower alkyl radicals such as methyl and ethyl radicals and radicals corresponding to the formula: $-R_{33}-N(R_{31})_2$, wherein $R_{33}$ is chosen from $-CH_2-CH_2-$, $-CH_2-CH_2-CH_2-$ and $-CH_2-CH(CH_3)-$ groups, $R_{31}$ is chosen from a hydrogen atom and lower alkyl radicals such as methyl and ethyl radicals and the higher homologues of these radicals and comprising up to 6 carbon atoms, and r is such that the molecular weight ranges from 500 to 6 000 000, for example, from 1000 to 1 000 000.

(8) Amphoteric polymers of the -D-X-D-X- type chosen from:

a) polymers obtained by the action of chloroacetic acid or sodium chloroacetate on compounds comprising at least one unit of formula:

$$-D-X-D-X-D-$$ (XXIII)

wherein D is a radical $$-N\diagup\diagdown N-$$

and X is chosen from symbols E and E', wherein E and E', which may be identical or different, are each chosen from divalent alkylene radicals comprising at least one chain chosen from linear and branched chains comprising up to 7 carbon atoms in the principal chain, wherein the divalent alkylene radicals are optionally substituted with at least one hydroxyl group. E or E' may comprise, in addition, at least one entity chosen from oxygen, nitrogen and sulphur atoms and 1 to 3-membered aromatic and heterocyclic rings; wherein the oxygen, nitrogen and sulphur atoms are present in the form of at least one group chosen from ether, thioether, sulphoxide, sulphone, sulphonium, alkylamine and alkenylamine groups, and hydroxyl, benzylamine, amine oxide, quaternary ammonium, amide, imide, alcohol, ester and urethane groups;

b) polymers of formula:

$$-D-X-D-X-$$ (XXIV)

wherein D is a radical $$-N\diagup\diagdown N-$$

and X is chosen from the symbols E or E' and, at least one X is chosen from E'; E having the meaning indicated above and E' is chosen from divalent alkylene radicals comprising at least one chain chosen from linear and branched chains comprising up to 7 carbon atoms in the principal chain, wherein the divalent alkylene radicals are optionally substituted with at least one hydroxyl radical. E' can also comprise at least one nitrogen atom, wherein the nitrogen atom is substituted with at least one alkyl chain optionally interrupted by at least one oxygen atom, wherein the alkyl chain comprises at least one functional group chosen from carboxyl functional groups and hydroxyl functional groups and wherein the alkyl chain is betainized by reaction with a reactant chosen from chloroacetic acid and sodium chloroacetate.

(9) The copolymers ($C_1$–$C_5$)alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

The at least one amphoteric polymer used in the compositions disclosed herein may, for example, be chosen from are those polymers of family (1).

The at least one amphoteric polymer may, for example, be present in an amount ranging from 0.01 % to 10% by weight, relative to the total weight of the composition, further, for example, from 0.05% to 5% by weight, relative to the total weight of the composition, and still further, for example, from 0.1% to 3% by weight, relative to the total weight of the composition.

The compositions disclosed herein may, for example, comprise at least one additional surfactant other than the $C_{10}$–$C_{14}$ fatty acids.

The at least one additional surfactant may, for example, be chosen from anionic, amphoteric, nonionic, zwitterionic and cationic surfactants.

The at least one additional surfactant suitable for use in the compositions disclosed herein may, for example, be chosen from the following:

(i) Anionic Surfactant(s):

The anionic surfactants which can be used in the compositions disclosed herein may, for example, be chosen from (non-limiting list) at least one of salts (for example, alkali metal, such as sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamidesulphonates, alkyl aryl sulphonates, α-olefinsulphonates, paraffinsulphonates; $(C_6$–$C_{24})$alkyl sulphosuccinates, $(C_6$–$C_{24})$alkyl ether sulphosuccinates, $(C_6$–$C_{24})$alkylamide sulphosuccinates; $(C_6$–$C_{24})$alkyl sulphoacetates; $(C_6$–$C_{24})$acyl sarcosinates and $(C_6$–$C_{24})$acyl glutamates. It is also possible to use $(C_6$–$C_{24})$alkyl polyglycoside carboxylic esters such as alkyl glucoside citrates, alkyl polyglycoside tartrate and alkyl polyglycoside sulphosuccinates, alkyl sulphosuccinamates; acyl isethionates and N-acyltaurates, the alkyl or acyl radical of all these various compounds, for example, comprising from 12 to 20 carbon atoms, and the aryl radical is chosen, for example, from phenyl and benzyl group.

The anionic surfactants can also be chosen, for example, from the salts of fatty acids such as the salts of oleic, ricinoleic, palmitic and stearic acids, the acids of copra oil and of hydrogenated copra oil; acyl lactylates whose acyl radical comprises from 8 to 20 carbon atoms. It is also possible to use alkyl D-galactoside uronic acids and salts thereof, polyoxyalkylenated $(C_6$–$C_{24})$alkyl ether carboxylic acids, polyoxyalkylenated $(C_6$–$C_{24})$alkylaryl ether carboxylic acids, polyoxyalkylenated $(C_6$–$C_{24})$alkyl amido ether carboxylic acids and salts thereof, for example, those comprising from 2 to 50 alkylene groups, such as ethylene, oxide groups, and mixtures thereof.

(ii) Nonionic Surfactant(s):

The nonionic surfactants may, for example, be chosen from compounds which are well known per se (in this respect see, for example, the "Handbook of Surfactants" by M. R. Porter, published by Blackie & Son (Glasgow and London), 1991, pp. 116–178) and, in the context of the present disclosure, their nature does not assume any critical character. The non-ionic surfactants can thus be chosen, for example, from (nonlimiting list) alpha-diols, polyethoxylated and polypropoxylated alkylphenols comprising at least one fatty chain comprising, for example, from 8 to 18 carbon atoms, it being possible for the number of ethylene oxide or propylene oxide groups to range, for example, from 2 to 50. Copolymers of ethylene oxide and propylene oxide and the condensates of ethylene oxide and propylene oxide with fatty alcohols may also be used in the compositions disclosed herein; polyethoxylated fatty amides, for example, comprising from 2 to 30 mol of ethylene oxide, polyglycerolated fatty amides comprising on average from 1 to 5 glycerol groups, for example, from 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as the oxides of $(C_{10}$–$C_{14})$-alkylamines and N-acylaminopropyl-morpholine oxides.

(iii) Amphoteric or Zwitterionic Surfactant(s):

The amphoteric or zwitterionic surfactants, the nature of which is not of critical importance in the compositions disclosed herein, may, for example, be chosen from (non-limiting list) derivatives of aliphatic secondary and tertiary amines wherein the aliphatic radical is chosen from linear and branched chains comprising from 8 to 18 carbon atoms and comprising at least one water-solubilizing anionic group (for example carboxylate, sulphonate, sulphate, phosphate and phosphonate); $(C_8$–$C_{20})$alkylbetaines, sulphobetaines, $(C_8$–$C_{20})$alkylamido$(C_1$–$C_6)$alkylbetaines and $(C_8$–$C_{20})$alkylamido$(C_1$–$C_6)$ alkylsulphobetaines may also be used.

The amine derivatives may, for example, be chosen from products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates having the respective structures:

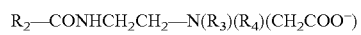

wherein:

$R_2$ is chosen from alkyl radicals of an acid $R_2$—COOH present in hydrolysed copra oil, and heptyl, nonyl and undecyl radicals, $R_3$ is chosen from beta-hydroxyethyl groups and $R_4$ is chosen from carboxymethyl groups; and

wherein:

B is chosen from —$CH_2CH_2OX'$ groups, C is chosen from —$(CH_2)_z$—Y' groups, wherein z=1 or 2, X' is chosen from —$CH_2CH_2$—COOH groups and a hydrogen atom, Y' is chosen from —COOH groups and radicals —$CH_2$—CHOH—$SO_3H$, and $R_2'$ is chosen from alkyl radicals of an acid $R_9$—COOH present in copra oil and in hydrolysed linseed oil, alkyl radicals, such as $C_7$, $C_9$, $C_{11}$, $C_{13}$, and $C_{17}$ alkyl radicals and iso form thereof and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauro-amphodipropionic acid, and Cocoamphodipropionic acid.

By way of example, cocoamphodiacetate marketed under the trade name MIRANOL® C2M concentrated by the company RHODIA CHIMIE can be used in the compositions disclosed herein.

(iv) Cationic Surfactants:

The cationic surfactants may, for example, be chosen from the following (nonlimiting list): the salts of optionally polyoxyalkylenated primary, secondary and tertiary amines; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives and amine oxides of a cationic nature.

The at least one additional surfactant may be present in the composition disclosed herein in an amount ranging, for example, from 0.01 to 40% by weight, relative to the total weight of the composition and further, for example, from 0.5 to 30% by weight, relative to the total weight of the composition.

Additional Thickening Agents

The compositions disclosed herein may also comprise other rheology adjusting agents such as at least one thickening agent. The at least one thickening agent may, for example, be chosen from cellulosic thickeners (hydroxyethylcellulose, hydroxypropylcellulose, carboxymethylcellulose, and the like), guar gum and derivatives thereof (hydroxypropylguar and the like), gums of microbial origin (xanthan gum, scleroglucan gum, and the like), synthetic thickeners such as crosslinked homopolymers of acrylic acid and acrylamidopropanesulphonic acid and ionic and non-ionic associative polymers such as the polymers marketed under the names PEMULEN® TR1 or TR2 by the company GOODRICH, SALCARE® SC90 by the company ALLIED COLLOIDS, ACULYN® 22, 28, 33, 44 and 46 by the company ROHM & HMS and ELFACOS® T210 and T212 by the company AKZO.

The at least one thickening agent may be present in an amount ranging, for example, from 0.01 to 10% by weight, relative to the total weight of the composition.

The appropriate dyeing medium for the composition disclosed herein may, for example, be an aqueous medium comprising water and may, for example, further comprise at least one cosmetically acceptable organic solvent. The at least one cosmetically acceptable organic solvent may, for example, be chosen from alcohols such as ethyl alcohol, isopropyl alcohol, benzyl alcohol and phenylethyl alcohol, glycols and glycol ethers such as, monomethyl, monoethyl and monobutyl ethers of ethylene glycol, propylene glycol and ethers thereof such as, monomethyl ether of propylene glycol, butylene glycol, dipropylene glycol as well as the alkyl ethers of diethylene glycol such as monoethyl ether and monobutyl ether of diethylene glycol. The at least one cosmetically acceptable organic solvent may, for example, be present in the compositions disclosed herein in an amount ranging from 0.5 to 20% by weight, relative to the total weight of the composition, and further, for example, from 2 to 10% by weight, relative to the total weight of the composition.

The at least one composition A may also comprise an effective quantity of at least one additional agent, previously known in oxidation dyeing, such as various customary adjuvants such as sequestrants such as EDTA and etidronic acid, UV-screening agents, waxes, volatile and nonvolatile silicones which are cyclic or linear or branched, optionally organomodified, for example with amine groups, preservatives, ceramides, pseudoceramides, vegetable, mineral and synthetic oils, vitamins and provitamins such as panthenol, opacifiers, associative polymers other than those disclosed herein, and, for example, nonionic associative polyether-polyurethanes.

The composition may also comprise at least one reducing agent and/or at least one antioxidant. The at least one reducing agent and/or the at least one antioxidant may be chosen, for example, from sodium sulphite, thioglycolic acid, thiolactic acid, sodium bisulphite, dehydroascorbic acid, hydroquinone, 2-methylhydroquinone, tert-butylhydroquinone and homogentisic acid, and the at least one reducing agent and the at least one antioxidant may, for example, be present in an amount ranging from 0.05 to 3% by weight, relative to the total weight of the composition.

Of course persons skilled in the art will be careful to choose the possible additional compound(s) mentioned above so that the advantageous properties intrinsically attached to the dyeing composition disclosed herein are not, or substantially not, impaired by the envisaged addition(s).

In the ready-to-use composition or in the at least one composition B, the at least one oxidizing agent may, for example, be chosen from urea peroxide, alkali metal bromates and ferricyanides, persalts such as perborates and persulphates. Hydrogen peroxide may, for example, be used in the compositions disclosed herein. This at least one oxidizing agent may, for example, comprise a solution of hydrogen peroxide whose titre may, for example, range from 1 to 40 volumes, and further, for example, from 5 to 40.

It is also possible to use at least one oxidizing agent chosen from oxidation-reduction enzymes such as laccases, peroxidases and oxidoreductases comprising 2 electrons (such as uricase), where appropriate in the presence of their respective donor or cofactor.

The pH of the ready-to-use composition applied to the keratin fibers [composition resulting from the mixture of the at least one dyeing composition A and of the at least one oxidizing composition B and optionally of the at least one composition C], ranges from 4 to 11. It may, for example range from 6 to 10, and may be adjusted to the desired value by means of at least one agent chosen from acidifying and alkalinizing agents well known in the state of the art for dyeing keratin fibers.

The alkalinizing agents may, for example, be chosen from aqueous ammonia, alkali metal carbonates, alkanolamines such as mono-, di- and triethanolamines and derivatives thereof, oxyethylenated and/or oxypropylenated ethylenediamines and hydroxyalkylamines, sodium and potassium hydroxides and compounds having the following formula (XXV):

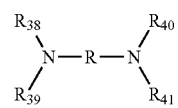

(XXV)

wherein R is chosen from propylene residues optionally substituted with at least one entity chosen from hydroxyl groups and $C_1$–$C_4$ alkyl radicals; $R_{38}$, $R_{39}$, $R_{40}$ and $R_{41}$, which may be identical or different, are each chosen from a hydrogen atom, $C_1$–$C_4$ alkyl and $C_1$–$C_4$ hydroxyalkyl radicals.

The acidifying agents may, for example, be chosen from conventional inorganic and organic acids such as hydrochloric acid, orthophosphoric acid, carboxylic acids such as tartaric acid, citric acid, lactic acid and sulphonic acids.

The dyeing method disclosed herein comprises applying a ready-to-use composition, freshly prepared at the time of use from the compositions A and B and optionally C described above, to the dry or wet keratin fibers, allowing it to act for an exposure time ranging, for example, from 1 to 60 minutes, further, for example, from 10 to 45 minutes, rinsing the fibers, and optionally washing the fibers with shampoo, and then in rinsing the fibers again, and in drying the fibers.

According to this method, the compositions A and/or B may further comprise at least one additional polymer chosen from cationic and amphoteric polymers and at least one additional surfactant.

A concrete example illustrating the composition disclosed herein is indicated below, without however exhibiting a limiting character.

EXAMPLE

The following compositions were prepared:
(quantities expressed in grams)

Oxidizing Composition:

| | |
|---|---|
| Cetylstearyl alcohol (80%)/cetylstearyl alcohol containing 30 EO (20%) mixture (SINNOWAX AO from COGNIS) | 2.35 g |
| Oleic acid diethanolamine | 0.95 g |
| Glycerin | 0.5 g |
| Hydrogen peroxide as a 50% solution in water | 12 g |
| Sequestering agent | 0.15 g |
| Stabilizing agents | 0.125 g |
| Perfume | qs |
| Acidifying agents | qs pH 2.8 |
| Demineralized water qs | 100 g |

| | |
|---|---|
| Natural lauric acid | 2.5 |
| Oxyethylenated lauryl alcohol (12 EO) | 7.5 |
| Cetylstearyl alcohol (C16/C18 50/50) | 10 |
| Glycol monosterate | 2 |
| Oxyethylenated oleocetyl alcohol (30 EO) | 3 |
| Oxyethylenated decyl alcohol (3 EO) | 10 |
| Pyrogenic silica with a hydrophobic character | 1 |
| Pure monoethanolamine | 1.2 |
| Dimethyl diallyl ammonium chloride homopolymer as a 40% aqueous solution | 7 |
| Propylene glycol | 10 |
| Terpolymer of vinylpyrrolidone, dimethyl-aminopropylmethacrylamide and lauryldimethyl-propylmethacrylamidoammonium chloride (74/15/11) | 4 |
| Crosslinked polyacrylic acid | 0.4 |
| Diethylenetriaminepentaacetic acid, pentasodium salt as a 40% aqueous solution | 2 |
| Ammonium thiolactate as a 58% aqueous solution (50% as thiolactic acid) | 0.8 |
| Mono-tert-butylhydroquinone | 0.3 |
| 1,4-diaminobenzene | 0.24 |
| 1-hydroxy-4-aminobenzene | 0.44 |
| 1-hydroxy-2-aminobenzene | 0.028 |
| 1,3-dihydroxybenzene (resorcinol) | 0.192 |
| 1-hydroxy-3-aminobenzene | 0.019 |
| 1-methyl-2-hydroxy-4-betahydroxyethylaminobenzene | 0.021 |
| 2-methyl-1,3-dihydroxybenzene (2-methylresorcinol) | 0.055 |
| Aqueous ammonia (at 20.5% of ammonia) | 10 |
| Perfume | 0.5 |
| Deionized water (qs) | qs 100 |

The polymer according to the present disclosure is a vinyl-pyrrolidone/dimethylaminopropylmethacrylamide/lauryldimethylmethacrylamidoammonium chloride terpolymer provided by the company ISP under the reference POLYMER ACP-1234.

The dyeing composition was mixed, at the time of use, in a plastic bowl and for 2 minutes, with the oxidizing composition given above, in an amount of 1 part of dyeing composition per 1.5 parts of oxidizing composition.

The mixture obtained was unctuous and was easy to prepare.

It was applied to natural grey hair which was 90% white. It was allowed to act for 30 minutes.

The product was easily removed by rinsing with water.

After washing with a standard shampoo, the hair was dried. It was then dyed in a golden blond shade.

When natural lauric acid was replaced by an equivalent amount of stearic acid, a mixture was obtained which was less easy to prepare, less pleasant to apply and which was more difficult to remove. The shade obtained was of an inferior quality.

What is claimed is:

1. A composition for the oxidation dyeing of keratin fibers, comprising, in an appropriate dyeing medium:
   at least one oxidation dye,
   at least one fatty acid chosen from $C_{10}$–$C_{14}$ fatty acids, and
   at least one cationic poly(vinyllactam) polymer comprising:
     at least one monomer (a) chosen from vinyllactam and alkylvinyllactam monomers and
     at least one monomer (b) chosen from monomers having the following structures (Ia) and (Ib):

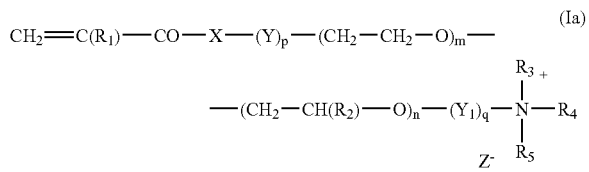

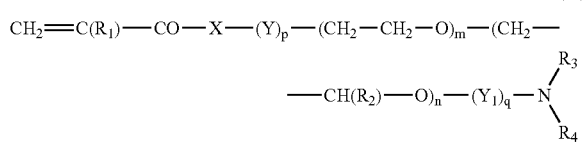

wherein:
   X is chosen from an oxygen atom and radicals $NR_6$,
   $R_1$ and $R_6$, which may be identical or different, are each chosen from a hydrogen atom and linear and branched $C_1$–$C_5$ alkyl radicals,
   $R_2$ is chosen from linear and branched $C_1$–$C_4$ alkyl radicals,
   $R_3$, $R_4$ and $R_5$, which may be identical or different, are each chosen from a hydrogen atom, linear and branched $C_1$–$C_{30}$ alkyl radicals and radicals of formula (II):

wherein
   Y, $Y_1$ and $Y_2$, which may be identical or different, are each chosen from linear and branched $C_2$–$C_{16}$ alkylene radicals,
   $R_7$ is chosen from a hydrogen atom, linear and branched $C_1$–$C_4$ alkyl radicals and linear and branched $C_1$–$C_4$ hydroxyalkyl radicals,
   $R_8$ is chosen from a hydrogen atom and linear and branched $C_1$–$C_{30}$ alkyl radicals,
   p, q and r, which may be identical or different, are each integers equal to either the value zero, or the value 1,
   m and n, which may be identical or different, are each integers ranging from 0 to 100,
   x is an integer ranging from 1 to 100, and $Z^-$ is chosen from organic and inorganic acid anions, provided that:
at least one of the substituents $R_3$, $R_4$, $R_5$ or $R_8$, is chosen from linear and branched $C_9$–$C_{30}$ alkyl radicals,
if m or n is different from zero, then q is equal to 1, and
if m or n are equal to zero, then p or q is equal to 0.

2. The composition according to claim 1, wherein the keratin fibers are hair.

3. The composition according to claim 1, wherein the at least one monomer chosen from vinyllactam and alkylvinyllactam monomers is a compound having the structure (III):

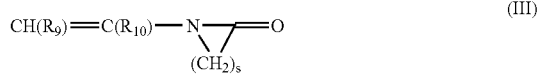

wherein:
s is an integer ranging from 3 to 6,
$R_9$ is chosen from a hydrogen atom and $C_1$–$C_5$ alkyl radicals, and
$R_{10}$ is chosen from a hydrogen atom and $C_1$–$C_5$ alkyl radicals, provided that at least one of the radicals $R_9$ and $R_{10}$ is a hydrogen atom.

4. The composition according to claim 3, wherein the at least one monomer of formula (III) is vinylpyrrolidone.

5. The composition according to claim 1, wherein, in formulae (Ia) or (Ib), the radicals $R_3$, $R_4$ and $R_5$, which may be identical or different, are each chosen from a hydrogen atom and linear and branched $C_1$–$C_{30}$ alkyl radicals.

6. The composition according to claim 1, wherein the at least one monomer (b) is chosen from monomers of formula (Ia).

7. The composition according to claim 6, wherein, in formula (Ia), m and n are equal to zero.

8. The composition according to claim 1, wherein the counterion $Z^-$ of the monomers of formula (Ia) is chosen from halide ions, phosphate ions, a metho-sulphate ion and a tosylate ion.

9. The composition according to claim 1, wherein the at least one cationic poly(vinyllactam) polymer comprises at least one additional monomer chosen from cationic and nonionic monomers.

10. The composition according to claim 9, wherein the at least one cationic poly(vinyllactam) is a terpolymer comprising:
(i) at least one monomer of formula (III),
(ii) at least one monomer of formula (Ia) wherein p=1, q=0, $R_3$ and $R_4$, which may be identical or different, are each chosen from a hydrogen atom and $C_1$–$C_5$ alkyl radicals and $R_5$ is chosen from $C_9$–$C_{24}$ alkyl radicals, and
(iii) at least one monomer of formula (Ib) wherein $R_3$ and $R_4$, which may be identical or different, are each chosen from a hydrogen atom and $C_1$–$C_5$ alkyl radicals.

11. The composition according to claim 10, wherein the terpolymer comprises, by weight, 40 to 95% of monomer (i), 0.25 to 50% of monomer (ii), and 0.1 to 55% of monomer (iii).

12. The composition according to claim 1, wherein the at least one cationic poly(vinyllactam) is chosen from following terpolymers:

vinylpyrrolidone/dimethylaminopropylmethacrylamide/dodecyldimethylmethacryl amidopropylammonium tosylate,
vinylpyrrolidone/dimethylaminopropylmethacrylamide/cocoyldimethyl-methacrylamidopropylammonium tosylate,
vinylpyrrolidone/dimethylaminopropylmethacrylamide/lauryl-dimethylmethacrylamidopropylammonium tosylate and
vinylpyrrolidone/dimethylaminopropylmethacrylamide/lauryl-dimethylmethacrylamidopropylammonium chloride.

13. The composition according to claim 1, wherein the weight-average molecular mass of the at least one cationic poly(vinyllactam) ranges from 500 to 20 000 000.

14. The composition according to claim 13, wherein the weight-average molecular mass of the at least one cationic poly(vinyllactam) ranges from 200 000 to 2 000 000.

15. The composition according to claim 14, wherein the weight-average molecular mass of the at least one cationic poly(vinyllactam) ranges from 400 000 to 800 000.

16. The composition according to claim 1, wherein the at least one cationic poly(vinyllactam) is present in an amount ranging from 0.01 to 10% by weight, relative to the total weight of the composition.

17. The composition according to claim 16, wherein the at least one cationic poly(vinyllactam) is present in an amount ranging from 0.1 to 5% by weight, relative to the total weight of the composition.

18. The composition according to claim 1, wherein the at least one fatty acid chosen from $C_{10}$–$C_{14}$ fatty acids is chosen from capric, lauric and myristic acids.

19. The composition according to claim 18, wherein the at least one fatty acid chosen from $C_{10}$–$C_{14}$ fatty acids is lauric acid.

20. The composition according to claim 1, wherein the at least one fatty acid chosen from $C_{10}$–$C_{14}$ fatty acids is present in an amount ranging from 0.1 to 40% by weight, relative to the total weight of the composition.

21. The composition according to claim 20, wherein the at least one fatty acid chosen from $C_{10}$–$C_{14}$ fatty acids is present in an amount ranging from 2 to 25% by weight, relative to the total weight of the composition.

22. The composition according to claim 21, wherein the at least one fatty acid chosen from $C_{10}$–$C_{14}$ fatty acids is present in an amount ranging from 5 to 20% by weight, relative to the total weight of the composition.

23. The composition according to claim 1, further comprising at least one oxidation dye chosen from oxidation bases and couplers.

24. The composition according to claim 23, wherein said at least one oxidation dye is chosen from at least one oxidation base.

25. The composition according to claim 24, wherein the at least one oxidation base is chosen from para-phenylenediamines, double bases, ortho- and para-aminophenols, and heterocyclic bases, and the acid addition salts thereof.

26. The composition according to claim 24, wherein the at least one oxidation base is present in an amount ranging from 0.0005 to 20% by weight, relative to the total weight of the composition.

27. The composition according to claim 23, wherein the at least one oxidation dye is chosen from at least one coupler.

28. The composition according to claim 27, wherein the at least one coupler is chosen from meta-phenylenediamines, meta-aminophenols, meta-diphenols, heterocyclic couplers, and the acid addition salts thereof.

29. The composition according to claim 28, wherein the at least one coupler is present in an amount ranging from 0.0001 to 20% by weight, relative to the total weight of the composition.

30. The composition according to claim 25, wherein the acid addition salts of the at least one oxidation base are chosen from hydrochlorides, hydrobromides, sulphates, tartrates, lactates and acetates.

31. The composition according to claim 28, wherein the acid addition salts of the at least one coupler are chosen from hydrochlorides, hydrobromides, sulphates, tartrates, lactates and acetates.

32. The composition according to claim 1, further comprising at least one direct dye.

33. The composition according to claim 1, further comprising at least one additional polymer chosen from at least one amphoteric polymer and at least one additional cationic polymer different from the at least one cationic poly(vinyllactam).

34. The composition according to claim 33, wherein the at least one additional cationic polymer is chosen from quaternary polyammonium polymers comprising recurring units corresponding to the following formula (W):

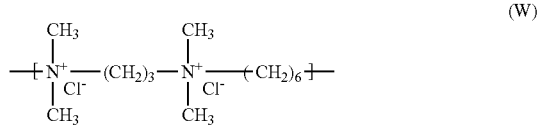

35. The composition according to claim 33, wherein the at least one additional cationic polymer is chosen from quaternary polyammonium polymers comprising recurring units corresponding to the following formula (U):

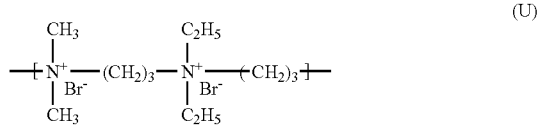

36. The composition according to claim 33, wherein the at least one amphoteric polymer is a copolymer chosen from monomers of at least one acrylic acid and at least one salt of dimethyldiallylammonium.

37. The composition according to claim 33, wherein the at least one additional polymer is present in an amount ranging from 0.01% to 10% by weight, relative to the total weight of the composition.

38. The composition according to claim 37, wherein the at least one additional polymer is present in an amount ranging from 0.05% to 5% by weight, relative to the total weight of the composition.

39. The composition according to claim 38, wherein the at least one additional polymer is present in an amount ranging from 0.1% to 3% by weight, of the total weight of the composition.

40. The composition according to claim 1, further comprising at least one surfactant chosen from anionic, cationic, nonionic and amphoteric surfactants.

41. The composition according to claim 40, wherein the at least one surfactant is present in an amount ranging from 0.01 to 40% by weight, relative to the total weight of the composition.

42. The composition according to claim 41, wherein the at least one surfactant is present in an amount ranging from 0.5 to 30% by weight, relative to the total weight of the composition.

43. The composition according to claim 1, further comprising at least one thickening agent.

44. The composition according to claim 1, further comprising at least one reducing agent present in an amount ranging from 0.05 to 3% by weight, relative to the total weight of the composition.

45. The composition according to claim 1, further comprising at least one oxidizing agent, wherein the composition is ready-for-use.

46. The composition according to claim 45, wherein the at least one oxidizing agent is chosen from hydrogen peroxide, urea peroxide, alkali metal bromates or ferricyanides, persalts, oxidation-reduction enzymes optionally with their respective donor or cofactor.

47. The composition according to claim 46, wherein the at least one oxidizing agent is hydrogen peroxide.

48. The composition according to claim 46, wherein the at least one oxidizing agent is a hydrogen peroxide solution whose titre ranges from 1 to 40 volumes.

49. The composition according to claim 45, wherein the pH of the ready-to-use composition ranges from 4 to 11.

50. A method for dyeing keratin fibers, comprising:
applying to the fibers at least one composition A comprising, in an appropriate dyeing medium, at least one oxidation dye,
developing the color at alkaline, neutral or acidic pH with the aid of at least one composition B comprising at least one oxidizing agent, which is mixed just at the time of use with the at least one composition A or which is applied sequentially without intermediate rinsing, wherein at least one fatty acid chosen from $C_{10}$–$C_{14}$ fatty acids is present in the at least one composition A and/or in the at least one composition B and at least one cationic poly(vinyllactam) polymer is present in the at least one composition A and/or in the at least one composition B, and wherein the at least one cationic poly(vinyllactam) comprises
at least one monomer (a) chosen from vinyllactam and alkylvinyllactam monomers and
at least one monomer (b) chosen from monomers having the following structures (Ia) and (Ib):

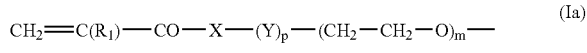

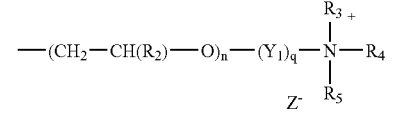

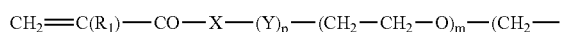

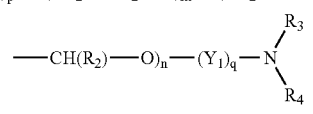

wherein:
X is chosen from an oxygen atom and radicals $NR_6$,
$R_1$ and $R_6$, which may be identical or different, are each chosen from a hydrogen atom and linear and branched $C_1$–$C_5$ alkyl radicals, $R_2$ is chosen from linear and branched $C_1$–$C_4$ alkyl radicals, $R_3$, $R_4$ and $R_5$, which may be identical or different, are each chosen from a hydrogen atom, linear and branched $C_1$–$C_{30}$ alkyl radicals and radicals of formula (II):

$$—(Y_2)_r—(CH_2—CH(R_7)—O)_x—R_8 \quad (II)$$

wherein, Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each integers equal to either the value zero, or the value 1, m and n, which may be identical or different, are each integers ranging from 0 to 100, x is an integer ranging from 1 to 100, and $Z^-$ is chosen from organic and inorganic acid anions, provided that:

at least one of the substituents $R_3$, $R_4$, $R_5$ or $R_8$, is chosen from linear and branched $C_9$–$C_{30}$ alkyl radicals, if m or n is different from zero, then q is equal to 1, and if m or n are equal to zero, then p or q is equal to 0.

51. The method according to claim 50, wherein the keratin fibers are hair.

52. The method according to claim 50, further comprising applying the ready-to-use composition, freshly prepared at the time of use from the compositions (A) and (B), to the dry or wet keratin fibers, allowing the ready-to-use composition to act for an exposure time ranging from 1 to 60 minutes, rinsing the fibers, optionally washing the fibers with shampoo, rinsing the fibers again, and drying the fibers.

53. A two-compartment device for dyeing keratin fibers comprising:

one compartment comprising at least one composition A1 comprising, in an appropriate dyeing medium, at least one oxidation dye, and a second compartment comprising at least one composition B1 comprising, in an appropriate dyeing medium, at least oxidizing agent, wherein at least one cationic poly(vinyllactam) is present in the at least one composition A1 and/or the at least one composition B1 and at least one fatty acid chosen from $C_{10}$–$C_{14}$ fatty acids is present in the at least one composition A1 and/or the at least one composition B1, and wherein the at least one cationic poly(vinyllactam) comprises at least one monomer (a) chosen from vinyllactam and alkylvinyllactam monomers and at least one monomer (b) chosen from monomers having the following structures (Ia) and (Ib):

$$CH_2{=}C(R_1)—CO—X—(Y)_p—(CH_2—CH_2—O)_m— \\ —(CH_2—CH(R_2)—O)_n—(Y_1)_q—\overset{R_3}{\underset{\underset{Z^-}{R_5}}{N^+}}—R_4 \quad (Ia)$$

-continued $$CH_2{=}C(R_1)—CO—X—(Y)_p—(CH_2—CH_2—O)_m—(CH_2— \\ —CH(R_2)—O)_n—(Y_1)_q—N\overset{R_3}{\underset{R_4}{{<}}} \quad (Ib)$$

wherein:

X is chosen from an oxygen atom and radicals $NR_6$, $R_1$ and $R_6$, which may be identical or different, are each chosen from a hydrogen atom and linear and branched $C_1$–$C_5$ alkyl radicals, $R_2$ is chosen from linear and branched $C_1$–$C_4$ alkyl radicals, $R_3$, $R_4$ and $R_5$, which may be identical or different, are each chosen from a hydrogen atom, linear and branched $C_1$–$C_{30}$ alkyl radicals and radicals of formula (II):

$$—(Y_2)_r—(CH_2—CH(R_7)—O)_x—R_8 \quad (II)$$

wherein, Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each integers equal to either the value zero, or the value 1, m and n, which may be identical or different, are each integers ranging from 0 to 100, x is an integer ranging from 1 to 100, and $Z^-$ is chosen from organic and inorganic acid anions, provided that:

at least one of the substituents $R_3$, $R_4$, $R_5$ or $R_8$, is chosen from linear and branched $C_9$–$C_{30}$ alkyl radicals, if m or n is different from zero, then q is equal to 1, and if m or n are equal to zero, then p or q is equal to 0.

54. The device according to claim 53, wherein the keratin fibers are hair.

55. A three-compartment device for dyeing keratin fibers comprising a first compartment comprising at least one composition A2 comprising, in an appropriate dyeing medium, at least one oxidation dye, a second compartment comprising at least one composition B2 comprising, in an appropriate dyeing medium, at least one oxidizing agent, and a third compartment comprising at least one composition C comprising, in an appropriate dyeing medium, at least one cationic poly(vinyllactam) comprising at least one monomer (a) chosen from vinyllactam and alkylvinyllactam monomers and at least one monomer (b) chosen from monomers having the following structures (Ia) and (Ib):

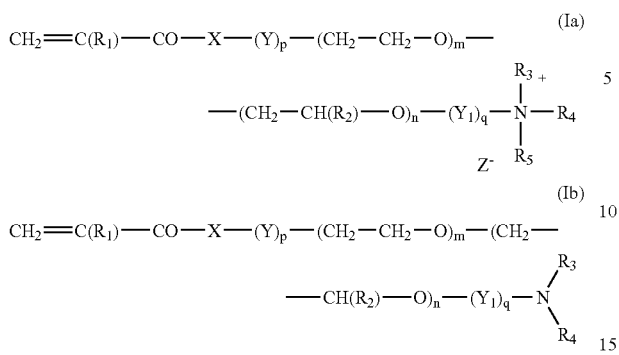

wherein:
- X is chosen from an oxygen atom and radicals $NR_6$,
- $R_1$ and $R_6$, which may be identical or different, are each chosen from a hydrogen atom and linear and branched $C_1$–$C_5$ alkyl radicals,
- $R_2$ is chosen from linear and branched $C_1$–$C_4$ alkyl radicals,
- $R_3$, $R_4$ and $R_5$, which may be identical or different, are each chosen from a hydrogen atom, linear and branched $C_1$–$C_{30}$ alkyl radicals and radicals of formula (II):

wherein, Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each integers equal to either the value zero, or the value 1, m and n, which may be identical or different, are each integers ranging from 0 to 100, x is an integer ranging from 1 to 100, and $Z^-$ is chosen from organic and inorganic acid anions, provided that:
at least one of the substituents $R_3$, $R_4$, $R_5$ or $R_8$, is chosen from linear and branched $C_9$–$C_{30}$ alkyl radicals, if m or n is different from zero, then q is equal to 1, and if m or n are equal to zero, then p or q is equal to 0, it being also possible for the at least one composition A2 and/or the at least one composition B2 to comprise the at least one cationic poly(vinyllactam) and it being also possible for the composition C to comprise at least one fatty acid chosen from $C_{10}$–$C_{14}$ fatty acids.

56. The kit according to claim 55, wherein the keratin fibers are hair.

* * * * *

UNITED STATES PATENT AND TRADEMARK OFFICE
CERTIFICATE OF CORRECTION

| | | |
|---|---|---|
| PATENT NO. | : 7,147,672 B2 | Page 1 of 1 |
| APPLICATION NO. | : 10/690696 | |
| DATED | : December 12, 2006 | |
| INVENTOR(S) | : François Cottard and Christine Rondeau | |

It is certified that error appears in the above-identified patent and that said Letters Patent is hereby corrected as shown below:

In claim 12, column 30, line 2, "dodecyidimethylmethacryl" should read

--dodecyldimethylmethacryl--.

Signed and Sealed this

Thirteenth Day of March, 2007

JON W. DUDAS
*Director of the United States Patent and Trademark Office*